(12) United States Patent
Lott et al.

(10) Patent No.: US 10,391,271 B2
(45) Date of Patent: Aug. 27, 2019

(54) APPARATUS FOR PERFORMING A CRICOTHYROTOMY/TRACHEOTOMY AND METHOD THEREFOR

(71) Applicants: David Lott, Scottsdale, AZ (US); Bryan Hooppaw, Scottsdale, AZ (US)

(72) Inventors: David Lott, Scottsdale, AZ (US); Bryan Hooppaw, Scottsdale, AZ (US)

( * ) Notice: Subject to any disclaimer, the term of this patent is extended or adjusted under 35 U.S.C. 154(b) by 348 days.

(21) Appl. No.: 15/354,125

(22) Filed: Nov. 17, 2016

(65) Prior Publication Data
US 2017/0136199 A1 May 18, 2017

Related U.S. Application Data

(60) Provisional application No. 62/256,439, filed on Nov. 17, 2015.

(51) Int. Cl.
| | | |
|---|---|---|
| *A61M 16/04* | (2006.01) | |
| *A61M 25/00* | (2006.01) | |
| *A61B 17/34* | (2006.01) | |
| *A61M 16/06* | (2006.01) | |

(52) U.S. Cl.
CPC ...... *A61M 16/0472* (2013.01); *A61M 16/044* (2013.01); *A61M 16/0411* (2014.02); *A61M 16/0497* (2013.01); *A61M 25/0082* (2013.01); *A61B 17/3496* (2013.01); *A61B 2017/3454* (2013.01); *A61M 16/0688* (2014.02); *A61M 2025/0095* (2013.01)

(58) Field of Classification Search
CPC .......... A61M 16/0472; A61M 16/0411; A61M 16/0497; A61M 2017/3454; A61M 17/3496; A61M 2025/0095
See application file for complete search history.

(56) References Cited

U.S. PATENT DOCUMENTS

| | | | | |
|---|---|---|---|---|
| 2,991,787 | A * | 7/1961 | Hunter .............. | A61M 16/0472 128/207.17 |
| 3,556,103 | A * | 1/1971 | Calhoun ........... | A61M 16/0472 128/200.26 |
| 5,487,731 | A * | 1/1996 | Denton ............. | A61M 16/0078 128/202.22 |
| 2009/0306697 | A1 * | 12/2009 | Fischvogt .......... | A61B 17/3421 606/185 |

* cited by examiner

*Primary Examiner* — Bradley J Osinski
(74) *Attorney, Agent, or Firm* — Weiss & Moy, P.C.; Jeffrey D. Moy

(57) ABSTRACT

A device and method for performing a cricothyrotomy and/or a tracheotomy has an outer cannula. An inner cutting cannula is positioned within the outer cannula. An actuator is coupled to a proximate end of the inner cutting cannula. The actuator keeps the inner cutting cannula in a retracted position within the outer cannula when the actuator is not activated and an extended position where a distal end of the inner cutting cannula extends out of the outer cannula with a force for the distal end of the inner cutting cannula to penetrate one of a cricothyroid membrane or tracheal wall when the actuator is activated.

14 Claims, 3 Drawing Sheets

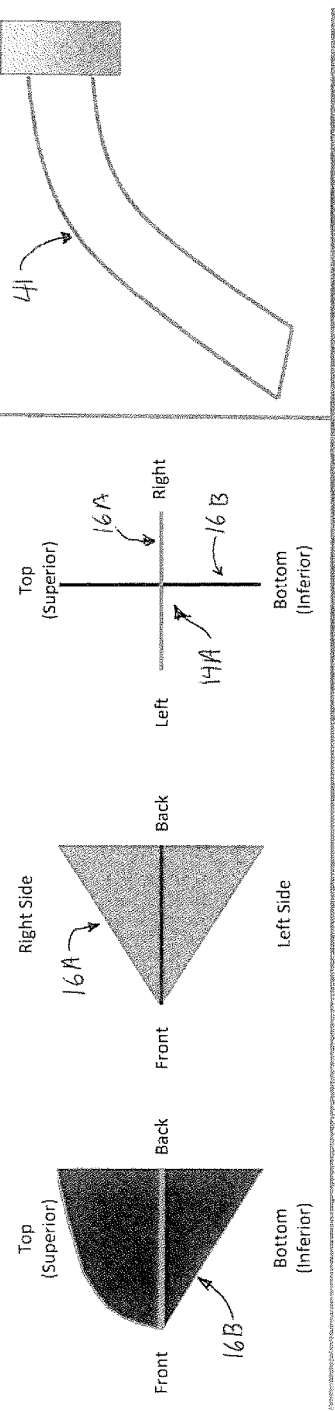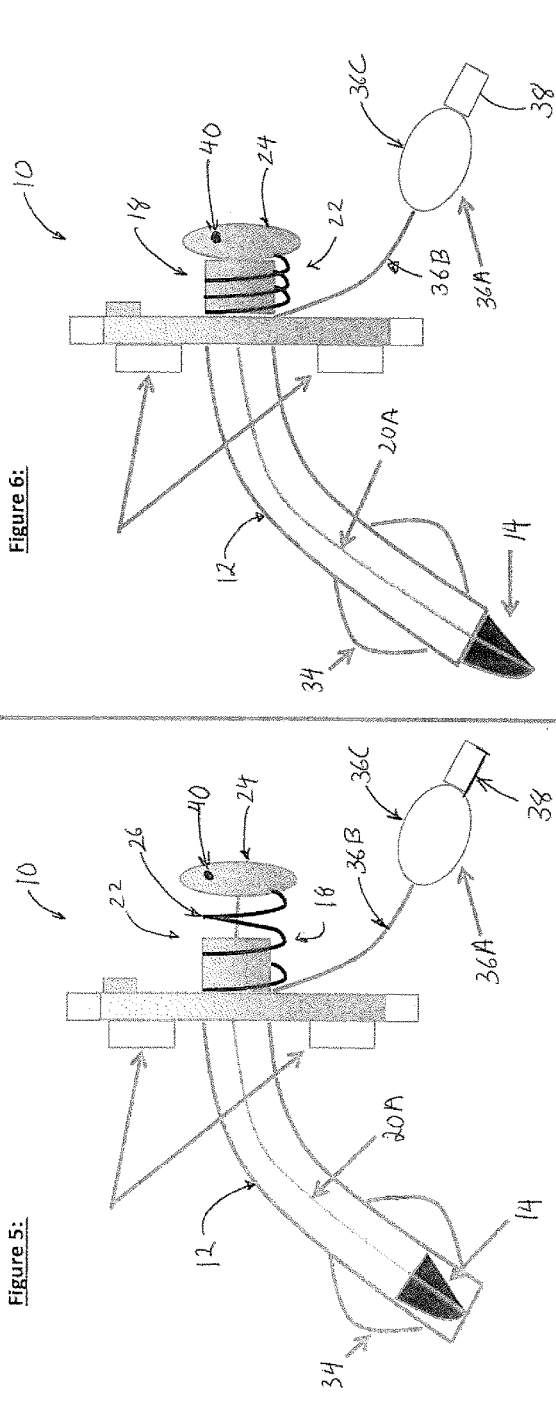

APPARATUS FOR PERFORMING A CRICOTHYROTOMY/TRACHEOTOMY AND METHOD THEREFOR

RELATED APPLICATIONS

The present patent application claims the benefit of U.S. Provisional Application No. 62/256,439, filed Nov. 17, 2015, entitled "APPARATUS FOR PERFORMING A CRICOTHYROTOMY/TRACHEOTOMY AND METHOD THEREFOR" in the name of the same inventors, and which is incorporated herein by reference in its entirety.

TECHNICAL FIELD

The present application generally relates to a medical device, and, more particularly, to an apparatus and method for performing a cricothyrotomy/tracheotomy involving placing the apparatus near the cricothyroid membrane or trachea of a person and depressing a firing mechanism that engages a cutting instrument to cut the cricothyroid membrane or trachea and smoothly place a tracheotomy tube into an airway of a person.

BACKGROUND

In emergent situations when an individual in unable to breathe, airway access is the primary concern. In the circumstance where there is an inability to place a breathing tube transorally (through the mouth), a surgical airway must be performed. Surgical access can be achieved through the cricothyroid membrane (cricothyrotomy) or trachea (tracheotomy). During these procedures, an incision is made on an anterior aspect of a neck of a person below an obstruction in order to open a direct airway. The opening serves as a site for insertion of a hollow tube (i.e., tracheotomy tube) into the opening. The hollow tube may allow the person to breathe without the use of his or her nose or mouth.

In these situations, time is of the essence and ease of surgical access is paramount. Unfortunately, the current standard procedure to perform a surgical airway either through the cricothyroid membrane or trachea contains multiple steps and multiple instruments. Additionally, many of these surgical airway procedures, especially when not performed in the hospital setting, are performed at night without adequate light for visualization. This complexity leads to delays in airway access or the complete inability to gain access to the airway in time to help the patient.

The standard procedure for access to the airway generally entails making a large incision over either the cricothyroid membrane or trachea. The incision is then continued down to the airway causing unneeded trauma to the surrounding structures and excessive bleeding. An incision is then made into the airway (cricothyroid membrane or trachea). The knife is removed from the airway, turned over, and the handle placed into the airway. This causes an unnecessary loss of contact with the newly found airway. A separate hook instrument is then used to secure the airway. The handle of the knife is then removed from the airway. The hand that was previously used to hold the knife grabs an endotracheal tube. The endotracheal tube is forced into the airway. There is no way to confirm proper placement of the endotracheal tube in the airway at the time of placement. A syringe is then needed to inflate the balloon on the endotracheal tube.

Once the patient is stable, the endotracheal tube has to be replaced with a tracheotomy tube. The tracheotomy tube has an indwelling inner cannula that allows for dilation of the airway as it is inserted. Once the tube is in place, the inner cannula is removed and a second hollow inner cannula is inserted. A syringe is needed to inflate the balloon on the tracheotomy tube. The tube is then secured to the patient's airway. There are numerous problems with this procedure. These issues include, but are not limited to: (1) the need for multiple steps; (2) excess time needed to perform multiple steps; (3) a large incision causing damage to surrounding structures and excess bleeding; (4) the potential for the incision to cause damage to vital structures; (5) the potential for the incision to go completely through the airway; (6) multiple steps where the person performing the procedure is not in contact with the airway; (7) the need for multiple instruments; (8) the need to grab a syringe to inflate the balloon; (9) the need to replace an endotracheal tube with a tracheotomy tube; (10) poor lighting and visualization; and (11) no confirmation that the tube is in the airway.

A second technique is used less frequently. This is called the Seldinger technique. With this technique, an incision is made through the skin above the airway. A needle is placed into the airway. A wire is placed through the needle into the airway. The needle is removed. A dilator is placed over the guide wire to dilate the airway so the tracheotomy tube can be placed. The tracheotomy tube is then placed over the guide wire. The guide wire is then removed. This procedure is also associated with many problems including, but not limited to: (1) the need for multiple steps; (2) excess time needed to perform multiple steps; (3) a large incision causing damage to surrounding structures and excess bleeding; (4) the potential of the needle to go completely through the airway; (5) multiple steps where the person performing the procedure is not in contact with the airway; (6) the need for multiple instruments; (7) the need to grab a syringe to inflate the balloon; (8) poor lighting and visualization; (9) blunt dilation of the airway causing excess damage; and (10) no confirmation that the tube is in the airway Therefore, it would be desirable to provide an apparatus and method that overcome the above problems.

SUMMARY

This summary is provided to introduce a selection of concepts in a simplified form that are further described below in the DESCRIPTION OF THE DISCLOSURE. This summary is not intended to identify key features of the claimed subject matter, nor is it intended to be used as an aid in determining the scope of the claimed subject matter.

In accordance with one aspect of the present disclosure, a device for performing a cricothyrotomy and/or a tracheotomy is disclosed. The device has an outer cannula. An inner cutting cannula is positioned within the outer cannula. An actuator is coupled to a proximate end of the inner cutting cannula and keeps the inner cutting cannula in a retracted position within the outer cannula. A distal end of the inner cutting cannula extending out of the outer cannula with a force for the distal end of the inner cutting cannula to penetrate one of a cricothyroid membrane or tracheal wall when the actuator is activated In accordance with one aspect of the present disclosure, a device for performing a cricothyrotomy and/or a tracheotomy is disclosed. The device has an outer cannula. The outer cannula is a curved hollow tubular conduit. A face plate is provided. An opening is formed in a central area of the face plate. The outer cannula is positioned through the opening and extends above a front surface of the face plate. An inner cutting cannula is positioned within the outer cannula. The inner cutting cannula comprises: a cutting mechanism; and a bar member, the cutting mechanism attached to a first end of the bar member. An actuator is coupled to a proximate end of the inner cutting cannula. The actuator keeps the cutting mechanism in a retracted position within the outer cannula. The cutting mechanism extending out of the outer cannula with a force for the cutting mechanism to penetrate one of a cricothyroid membrane or tracheal wall when the actuator is activated.

In accordance with one aspect of the present disclosure, a device for performing a cricothyrotomy and/or a tracheotomy is disclosed. The device has an outer cannula. The outer cannula is a curved hollow tubular conduit. A face plate is provided. An opening is formed in a central area of the face plate. The outer cannula is positioned through the opening and extends above a front surface of the face plate. An inner cutting cannula is positioned within the outer cannula. The inner cutting cannula comprises: a cutting mechanism, wherein the cutting mechanism comprises: a pair of blades oriented in a horizontal direction; and a pair of guide members oriented in a vertical directions; wherein superior aspects of the pair of guide members are curved; and a bar member, the cutting mechanism attached to a first end of the bar member. An actuator is coupled to a second end of the bar member. The actuator keeps the cutting mechanism in a retracted position within the outer cannula. The cutting mechanism extends out of the outer cannula with a force for the cutting mechanism to penetrate one of a cricothyroid membrane or tracheal wall when the actuator is activated. An occlusive balloon is coupled to an inferior end of the outer cannula. An air source is coupled to the occlusive balloon, wherein the air source comprises: a gas cartridge; and a syringe port attached to the gas cartridge.

BRIEF DESCRIPTION OF THE DRAWINGS

The present application is further detailed with respect to the following drawings. These figures are not intended to limit the scope of the present application but rather illustrate certain attributes thereof.

FIGS. 4a-4c demonstrates an arrowhead knife that is situated at the end of the inner knife plunger of an exemplary apparatus for performing a tracheotomy/cricothyrotomy in accordance with one aspect of the present application;

FIG. 5 shows the outer cannula with the inner knife plunger in place but not depressed for an exemplary apparatus for performing a tracheotomy/cricothyrotomy in accordance with one aspect of the present application;

FIG. 6 shows the outer cannula with the inner knife plunger depressed for an exemplary apparatus for performing a tracheotomy/cricothyrotomy in accordance with one aspect of the present application;

FIG. 7 demonstrates the inner cannula that is placed into the outer cannula once the patient is stable for an exemplary apparatus for performing a tracheotomy/cricothyrotomy in accordance with one aspect of the present application;

DESCRIPTION OF THE APPLICATION

Figure 1:
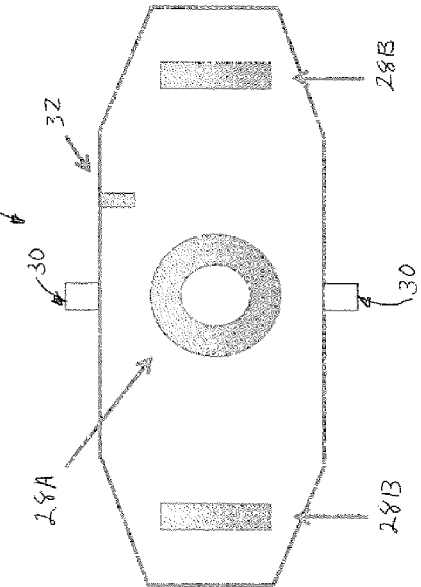
FIG. 1 shows an outer cannula of an exemplary apparatus for performing a tracheotomy/cricothyrotomy in accordance with one aspect of the present application.
Figure 2:
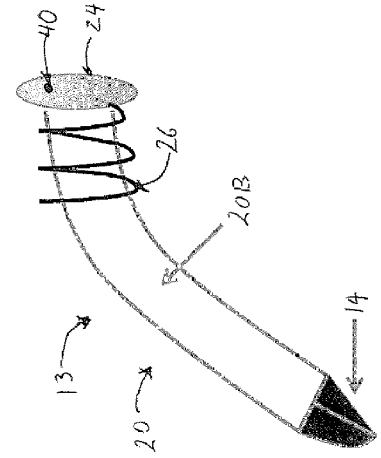
FIG. 2 shows an anterior (front) view of a faceplate of an exemplary apparatus for performing a tracheotomy/cricothyrotomy in accordance with one aspect of the present application.

The description set forth below in connection with the appended drawings is intended as a description of presently preferred embodiments of the disclosure and is not intended to represent the only forms in which the present disclosure may be constructed and/or utilized. The description sets forth the functions and the sequence of steps for constructing and operating the disclosure in connection with the illustrated embodiments. It is to be understood, however, that the same or equivalent functions and sequences may be accomplished by different embodiments that are also intended to be encompassed within the spirit and scope of this disclosure.

Referring to the Figures, a device 10 for performing a tracheotomy and/or cricothyrotomy will be disclosed. The device 10 was designed to overcome the numerous problems that were previously described. The device 10 may allow for one step access to the airway thereby negating the need for a large incision and its associated problems. The person performing the procedure in general will never lose contact with the airway. An incision only the size of the tracheotomy tube may be made thereby minimizing damage to the airway and surrounding structures. The specialized arrowhead blade design encompasses a guide that may prevent the device 10 from completely cutting through the back wall of the airway. A $CO_2$ cartridge may be used for instant inflation of a balloon without the need of a syringe. The device 10 may include a $CO_2$ indicator/monitoring sensor to ensure proper placement of the device within an airway of the patient. The device 10 may include a lighting unit to aid in visualization when performing a tracheotomy. The device 10 may be used at any location in the upper airway, any age, and on animals. The device 10 may be used in the emergent environment or as a routine placement of a tracheotomy tube. The above, as well as other features will be disclosed below.

The device 10 may have an outer cannula 12. The outer cannula 12 may be a hollowed conduit. The outer cannula 12 may be tubular in nature and may have a slight curve or bend formed therein. The slight curved nature of the outer cannula 12 may allow the outer cannula 12 to be inserted into a tracheostomy/cricothyrotomy stoma (the hole made in the neck and windpipe (trachea/cricothyroid membrane)) when the device 10 is used during a tracheotomy/cricothyrotomy. The outer cannula 12 may come in various sizes standard for tracheotomy tubes.

Located within the outer cannula 12 may be an inner cutting cannula 13. The inner cutting cannula 13 may be formed of a cutting mechanism 14. The cutting mechanism 14 may be used to penetrate skin and the cricothyroid membrane or tracheal wall of the patient. The cutting mechanism 14 may be designed to be extended from and retracted into the outer cannula 12. This may allow the cutting mechanism 14 to be held within the outer cannula 12 to prevent accidental cutting of individuals when the device 10 is not in use. When the device 10 is in use, the cutting mechanism 14 may be deployed to penetrate the skin and the cricothyroid membrane or tracheal wall of the subject. The cutting mechanism 14 may be designed to limit the extension of the cutting mechanism 14 to prevent the cutting mechanism 14 from puncturing the back wall of the posterior aspect of the airway.

In accordance with an embodiment, the cutting mechanism 14 may be formed of a cutting blade 14A. In accordance with one embodiment, the cutting blade 14A may be designed to have a blade 16A oriented in a horizontal direction and guides 16B in a vertical direction. The horizontal orientation of the blade 16A may allow for incision in the anatomic plane of the cricothyroid membrane/tracheal cartilages. The guides 16B may dilate the airway during insertion to allow entrance of the tube and guides the blade away from the posterior wall of the cricoid/trachea, thereby providing another layer of protection in emergent situations against misplacement through the posterior aspect of the airway. In accordance with one embodiment, the guide 16B may be formed of a hardened plastic material.

In the present embodiment, the cutting mechanism 14 is formed in the shape of an arrowhead. The cutting blade 16A and the guides 16B may be four separate flanges tapering from a point at the front of the cutting mechanism 14 and expanding to the size of the outer cannula 12 at the back of the cutting mechanism. The superior aspect of the guide 16B may be curved to deflect the cutting blade 16A into the airway and away from the posterior wall of the cricoid/trachea. While not shown, the inferior portion of the guide 16B may be curved to improve dilation. In an alternative embodiment, the cutting mechanism 14 may be formed in the shape of an arrowhead wherein the horizontal and vertical portions are cutting blades 16A.

The cutting mechanism 14 may be positioned on a plunger mechanism 18 and inserted into the outer cannula 12. The plunger mechanism 18 may be used to allow the cutting mechanism 14 to move from a retracted restrained position within the outer cannula 12 to an extended operational position outside of the outer cannula 12 with sufficient force to penetrate the cricothyroid membrane or tracheal wall.

Figure 3A:
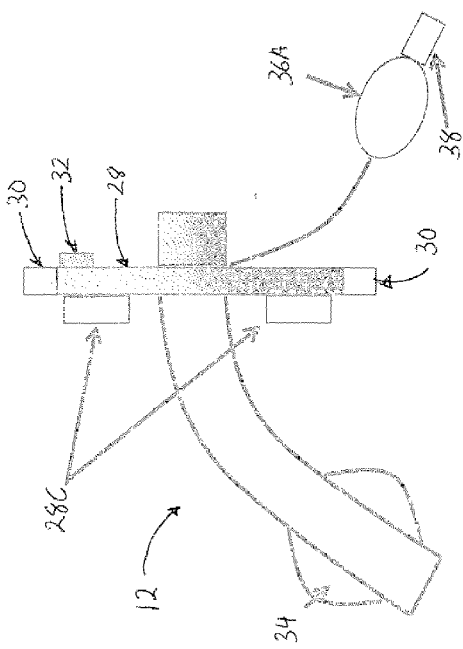
FIG. 3a shows one embodiment of a removable/retractable inner knife plunger of an exemplary apparatus for performing a tracheotomy/cricothyrotomy in accordance with one aspect of the present application.

In accordance with one embodiment, the plunger mechanism 18 may be formed of a bar member 20. The bar member 20 may be formed of a rigid metal or plastic material. The bar member 20 may have a slight bend/curve similar to that of the outer cannula 12. As may be seen in FIG. 3a, the bar member 20 may be a nonmalleable wire 20A. Alternatively, the bar member 20 may be a hollow cannula 20B having a circumference approximately that of the cutting mechanism 14.

The cutting mechanism 14 may be attached to one end of the bar member 20. An actuator 22 may be coupled to an opposing end of the bar member 20. The actuator 22 may be used to move the cutting mechanism 14 from the retracted restrained position within the outer cannula 12 to the extended operational position outside of the outer cannula 12 with sufficient force to penetrate the cricothyroid membrane or tracheal wall. In accordance with one embodiment, the actuator 22 may be a spring loaded actuator. The spring loaded actuator may have a depressible button 24 coupled to the bar member 20. A coil mechanism 26 may be positioned between the depressible button 24 and a face plate 28 and wraps around the bar member 20. The coil mechanism 26 may exert sufficient force to move and keep the cutting mechanism 14 in a retracted restrained position within the outer cannula 12. However, pressing the depressible button 24 with sufficient force may move the cutting blade 16 to an extended operational position outside of the outer cannula 12. When the depressible button 24 is pressed with sufficient force, the cutting blade 16 may extend out of the outer cannula 12 so that a widest part of the cutting mechanism 14 is at an edge of the outer cannula 12 and penetrates the cricothyroid membrane or tracheal wall.

The face plate 28 may extend from the sides of the outer cannula 12. The entrance of the outer cannula 12 extrudes just beyond the faceplate 28 as it is seen on a standard tracheotomy tube to allow for the attachment of a ventilation device if needed. The face plate 28 may have a central opening 28A to allow air flow to and from the outer cannula 12. The holds 28B may be formed on opposing ends of the face plate 28. The tie holds 28B may be used to attach cloth ties or velcro strap around the neck of the patient. A sticky tape 28C may be affixed to the lateral aspects of the under surface of the faceplate 28 to stick to the skin.

A lighting instrument 30 may be formed on the face plate 28. The lighting instrument 30 may be used to illuminate the neck area when performing a procedure. The lighting instrument 30 may be formed on one or both of the superior and inferior aspects of the face plate 28. The lighting instrument 30 may be formed of a Light Emitting Diode (LED) light and a power source. A switch 32 may be used to activate and deactivate the lighting instrument 30. The switch 32 may be one or both of the superior and inferior aspects of the face plate 28.

The device 10 may have an occlusive balloon 34 formed on a bottom inferior end of the outer cannula 12. The occlusive balloon 34 may be used to fill the tracheal space around the outer cannula 12 and prevent breath from escaping through the upper airway. The inflated occlusive balloon 34 may prevent leakage of air and ensuring a consistent delivery of air. The occlusive balloon 34 may be in gaseous communication with an air source 36A. In the embodiment shown, a tubing 36B may be used to connect the occlusive balloon 34 with the air source 36A. The air source may be a deployable $CO_2$ cartridge 36C, an air pump bladder or similar air source devices. A $CO_2$ cartridge 36C may provide an instant fill of the occlusive balloon 34 which may be helpful in exigent circumstances. In accordance with one embodiment, the $CO_2$ cartridge 36C may have a syringe port 38 attached thereto. The syringe port 38 may allow one to fine-tune the pressure of the occlusive balloon 34 with a syringe if needed once time allows.

In accordance with one embodiment, the device 10 may have a $CO_2$ indicator/monitor 40 located on the plunger mechanism 18. The $CO_2$ indicator/monitor 40 may confirm placement of the outer cannula 12 within the airway by monitoring the presence of or levels of $CO_2$ traveling through the outer cannula 12.

The device 10 may have an inner cannula 41. The inner cannula 41 may be placed into the outer cannula 12 once the patient is stable. This helps with cleaning of the tubes when it is in place long-term.

In the case of a difficult to identify cricothyroid membrane/trachea, a disarticulating needle catheter 42 may be used. The disarticulating needle catheter 42 may have an inner needle 44. The inner needle 44 may be various gauges in size (typically between 12-16 gauge in size) and has a hub 46 for attachment to a syringe. An outer disarticulating catheter 48 is sized to house the inner needle 44. The outer catheter 48 may have a disarticulating head 50 that opens to allow placement of the cutting mechanism 14 within the outer disarticulating needle catheter 48, following the removal of the inner needle 44. The outer disarticulating catheter 48 may have ridges 51 to guide the cutting mechanism 14 through the housing of the outer disarticulating catheter 48 as the cutting mechanism 14 cuts it open for placement into the airway. Handles/grips 52 may be formed on the disarticulating head 50 to open the outer disarticulating catheter 48.

Figure 3B:
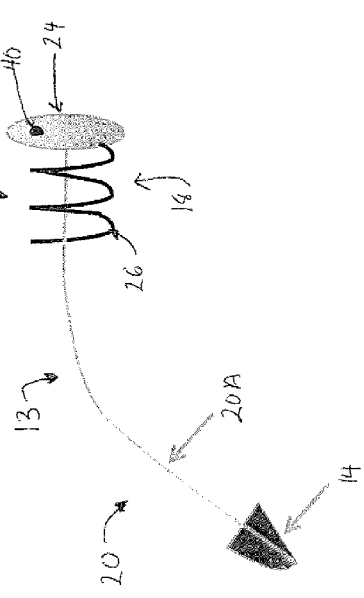
FIG. 3b shows one embodiment of a removable/retractable inner knife plunger of an exemplary apparatus for performing a tracheotomy/cricothyrotomy in accordance with one aspect of the present application.

Referring to the Figures, operation of the device 10 will be disclosed. The device 10 may come preloaded with the removable/retractable inner cutting cannula 13 (FIG. 3) and attached cutting mechanism 14 (FIG. 4) inside the outer cannula 12 as seen in FIG. 5. The lighting instrument 30 may be turned on via the switch 32 to illuminate the neck area when performing a procedure. The user of the device 10 may locate a cricothyroid membrane or trachea on the patient.

The device 10 may be grabbed with the hand of the user. In one smooth motion, the user may depress the actuator 22 with the thumb of the user to move the cutting mechanism 14 to an extended operational position outside of the outer cannula 12. When the depressible button 24 is pressed with sufficient force, the cutting mechanism 14 may extend out of the outer cannula 12 as shown in FIG. 6 and penetrate the cricothyroid membrane or tracheal wall. The tapered nature of the cutting mechanism 14 may create an incision only of the size needed for insertion of the outer cannula 12. The plastic guides 16B of the cutting mechanism 14 may dilate the airway during insertion to allow entrance of the outer cannula 12 and guides the blade away from the posterior wall of the cricoid/trachea, thereby providing another layer of protection in emergent situations against misplacement through the posterior aspect of the airway.

The outer cannula 12 may then be smoothly placed into the airway. Once in the airway, the thumb is removed from the depressible button 24 resulting in retraction of the cutting mechanism 14 back to its resting state as seen in FIG. 5. The user may confirm proper placement in the airway if needed with the $CO_2$ indicator/monitor 44 on/within the actuator 22. The $CO_2$ indicator/monitor 40 confirms placement of the outer cannula 12 within the airway. The $CO_2$ cartridge 36A may be deployed causing inflation of the occlusive balloon 34 to the correct size and pressure. This may negate the need to reach for a syringe. A separate syringe can be attached to the syringe port 38 and used to inflate the occlusive balloon 34 if needed. The inner cutting cannula 13 may then be removed from the outer cannula 12. The user may then secure the face plate 28 to the patient's neck. In some versions of the device 10, the faceplate 28 can stick to the skin fixing the outer cannula 12 in place until a tie can be placed, thereby preventing displacement.

Figure 8:
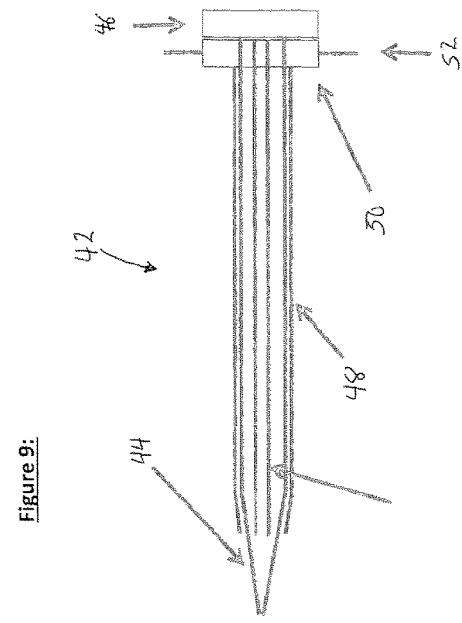
FIG. 8 demonstrates the components of the disarticulating needle catheter that is used when the airway is difficult to find for an exemplary apparatus for performing a tracheotomy/cricothyrotomy in accordance with one aspect of the present application.
Figure 9:
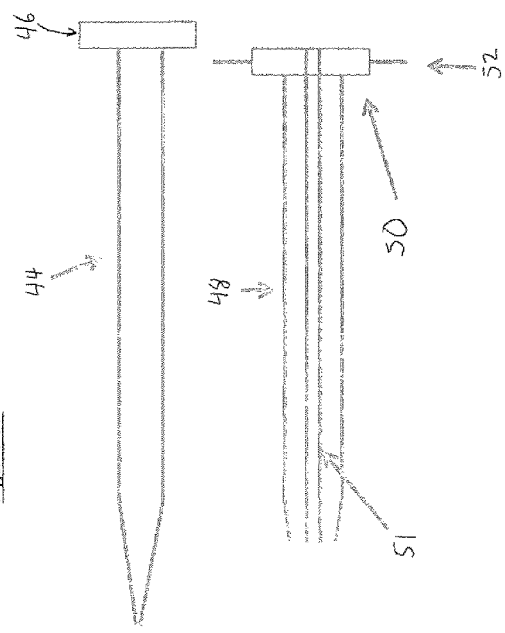
FIG. 9 shows the inner needle and outer disarticulating catheter together for an exemplary apparatus for performing a tracheotomy/cricothyrotomy in accordance with one aspect of the present application.
Figure 11:
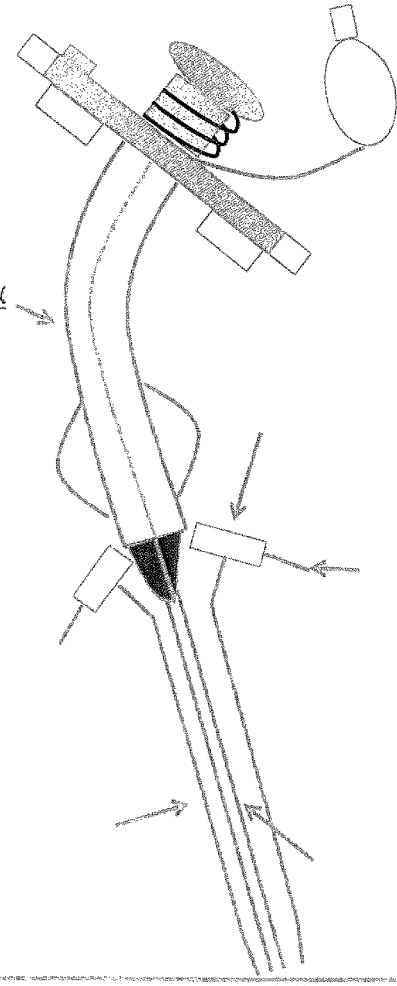
FIG. 11 demonstrates the arrowhead knife and tracheotomy tube using the outer disarticulating catheter as a guide for placement into the airway for an exemplary apparatus for performing a tracheotomy/cricothyrotomy in accordance with one aspect of the present application.
Figure 10:
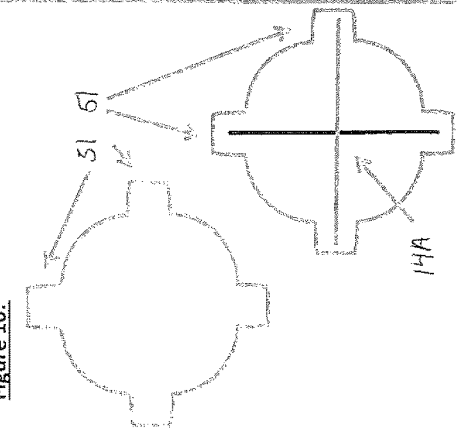
FIG. 10 shows the front view of the ridges on the outer disarticulating catheter that are used to guide the arrowhead knife through the housing of the catheter for an exemplary apparatus for performing a tracheotomy/cricothyrotomy in accordance with one aspect of the present application.

In the case of a difficult to identify cricothyroid membrane/trachea, a disarticulating needle catheter 42 (FIGS. 8-11) can be used. The disarticulating needle catheter 42 (FIG. 9) may be attached to a 3 mL syringe with 2 mL of saline in the syringe via the hub 46. The inner needle 44 may be placed into the neck and the plunger of the syringe is retracted until air bubbles (from the patient's airway) are seen in the syringe, confirming placement of the needle catheter 44 into the airway. The needle catheter 44 and syringe are removed from the outer disarticulating catheter 48 (FIG. 8). The outer disarticulating catheter 48 may be left in the airway to guide placement of the outer cannula 12 (tracheotomy tube) into the airway. Handle grips 52 attached to the head of the outer catheter 48 may be used to disarticulate the head 54 (FIG. 11). As described above, the inner cutting cannula 13 is depressed causing it to extrude from the outer cannula 12 (i.e., tracheotomy tube) (FIG. 6). The arrowhead configuration of the cutting mechanism 14 fits into the ridges 50 of the outer catheter 48 and assist in guiding the cutting mechanism 14 into the airway (FIG. 10, 11). The cutting mechanism 14 cuts the side ridges 50 open as it advances allowing for removal of the outer cannula 48. Once the outer cannula 14 (i.e., tracheotomy tube) is confirmed in the airway as described, the outer catheter 48 is removed.

While embodiments of the disclosure have been described in terms of various specific embodiments, those skilled in the art will recognize that the embodiments of the disclosure may be practiced with modifications within the spirit and scope of the claims.

What is claimed is:

1. A device for performing a cricothyrotomy and/or a tracheotomy comprising:
    an outer cannula;
    an inner cutting cannula positioned within the outer cannula;
    an actuator coupled to a proximate end of the inner cutting cannula, the actuator keeping the inner cutting cannula in a retracted position within the outer cannula, a distal end of the inner cutting cannula extending out of the outer cannula with a force to allow for the distal end of the inner cutting cannula to penetrate one of a cricothyroid membrane or tracheal wall when the actuator is activated;
    a disarticulating needle catheter positioned at a distal end of the outer cannula wherein the disarticulating needle catheter comprises:
    a needle; and
    an outer catheter housing the needle, the outer catheter having a disarticulating head that opens to allow the inner cutting cannula within the outer catheter when the needle is removed.

2. The device of claim 1, comprising:
    a face plate;
    an opening formed in a central area of the face plate, the outer cannula positioned through the opening and extending above a front surface of the face plate.

3. The device of claim 2, comprising tie holds formed on opposing side ends of the face plate.

4. The device of claim 2, comprising an adhesive material coupled to a bottom surface of the face plate.

5. The device of claim 2, comprising a lighting instrument formed on the face plate.

6. The device of claim 1, comprising:
    an occlusive balloon coupled to an inferior end of the outer cannula; and
    an air source coupled to the occlusive balloon.

7. The device of claim 6, wherein the air source comprises:
    a gas cartridge; and
    a syringe port attached to the gas cartridge.

8. The device of claim 1, comprising a carbon dioxide ($CO_2$) indicator/monitor coupled to the inner cutting cannula.

9. The device of claim 1, comprising an inner cannula positioned within the outer cannula after the inner cutting cannula is removed.

10. The device of claim 1, wherein the inner cutting cannula comprises:
   a cutting mechanism;
   a bar member, the cutting mechanism attached to a first end of the bar member, the actuator coupled to a second end of the bar member.

11. The device of claim 10, wherein the cutting mechanism comprises:
   a blade oriented in a horizontal direction; and
   guide members attached to the blade and oriented in a vertical directions.

12. The device of claim 10, wherein the cutting mechanism is formed in a shape of an arrowhead, the cutting mechanism tapering from a point at a front of the cutting mechanism and expanding to a size of a width of the outer cannula.

13. The device of claim 12, wherein the cutting mechanism comprises:
   a pair of blades oriented in a horizontal direction; and
   a pair of guide members oriented in a vertical directions.

14. The device of claim 1, wherein the actuator is a spring loaded actuator.

* * * * *